United States Patent [19]

Karcher et al.

[11] Patent Number: 4,751,389

[45] Date of Patent: Jun. 14, 1988

[54] MULTIPLE DETECTOR FOR TOMOGRAPHY

[75] Inventors: Gilles Karcher, Nancy; Max Amor, Vandoeuvre; Roger Niddam, Le Rancy, Jean-Pierre Villemot, Nancy, all of France

[73] Assignee: Medicorp Research Laboratories Corporation, Boca Raton, Fla.

[21] Appl. No.: 831,350

[22] Filed: Feb. 20, 1986

[30] Foreign Application Priority Data

Feb. 20, 1985 [FR] France ................................ 85 02427

[51] Int. Cl.⁴ ............................................ G01T 1/166
[52] U.S. Cl. ................................ 250/363 R; 250/366; 250/367; 250/369
[58] Field of Search .................... 250/363 SB, 363 SC, 250/366, 367, 368, 363 SA; 250/369

[56] References Cited

U.S. PATENT DOCUMENTS 3,793,520  2/1974  Grenier ................................ 250/368
4,095,107  6/1978  Genna et al. ................. 250/363 SB Primary Examiner—Carolyn E. Fields
Attorney, Agent, or Firm—Darby & Darby

[57] ABSTRACT

Elementary detectors constituted by juxtaposed crystals are scanned by two groups of photomultipliers: photomultipliers of energy each scanning an elementary detector and photomultipliers of rank each one scanning a crystal of predetermined rank in each of the elementary detectors. All the photomultipliers are connected to the primary computer.

6 Claims, 1 Drawing Sheet

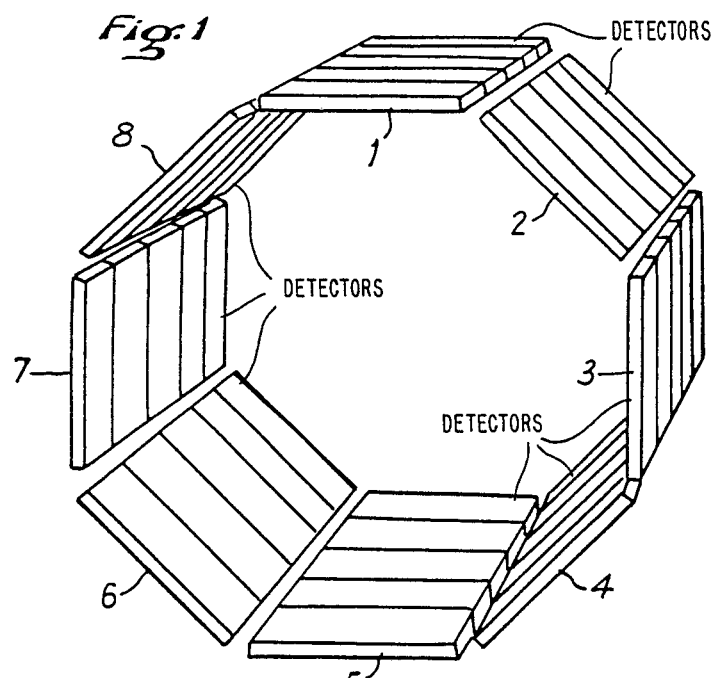
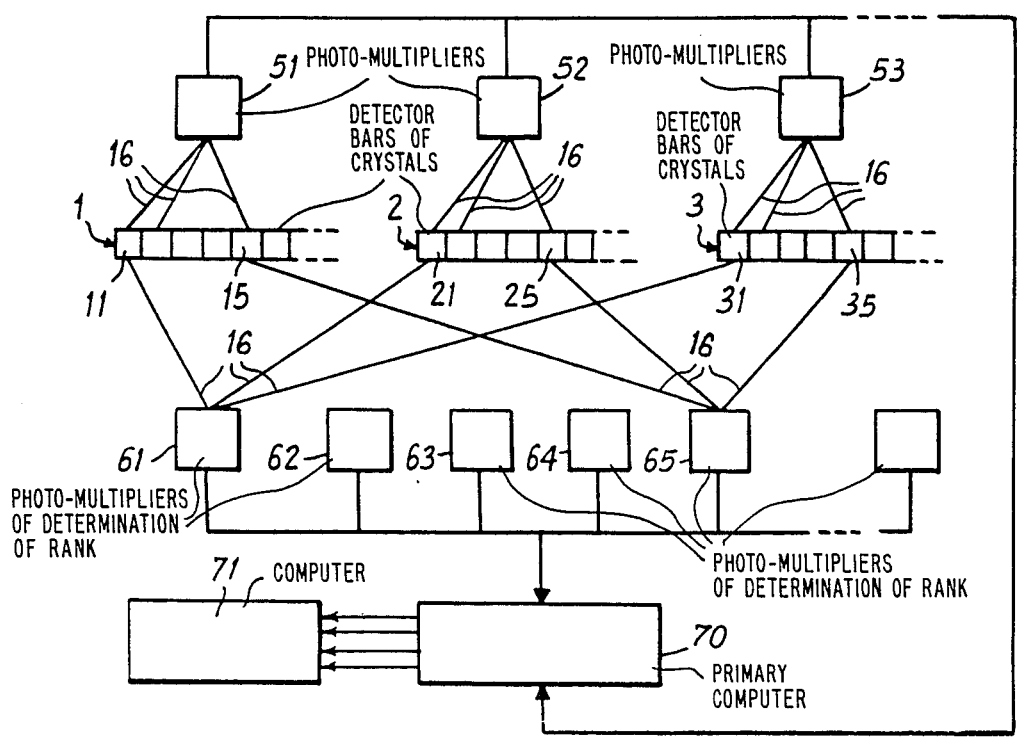

MULTIPLE DETECTOR FOR TOMOGRAPHY

FIELD OF THE INVENTION

The invention relates to a multiple detector for tomoscintigraphy.

BACKGROUND OF THE PRIOR ART

To study an organ such as the heart, brain or liver in tomoscintigraphy, it is common practice to use a rotating gamma-camera with single-incidence sensitive monocrystal. The gamma-camera has a wide field (about 40 cm), and excellent spatial resolution and linearity. But the gamma-camera has to make one measurement for each incidence selected and consequently the time for acquisition of the data needed to reconstruct images of the organ observed is very long.

One aim of the present invention is to become independent of the gamma-camera in tomoscintigraphy and to obtain in one action, all the data corresponding to each section and each incidence, by utilizing the fact that the radioactive emission is isotropic.

Another aim of the invention is to provide a special arrangement and coupling of the measuring apparatus used, in order to reduce the number thereof.

SUMMARY OF THE PRESENT INVENTION

The subject of the invention is a multiple detector for tomoscintigraphy, of the single-incidence sensitive, crystal type, comprising elementary detectors whose number corresponds to the product of the number of incidences times the number of sections in order to receive, simultaneously, all the incidences of all the sectios desired, each elementary detector being constituted by a bar comprising a certain number of crystals juxtaposed and oriented to receive one incidence of a predetermined section, characterized in that it comprises two groups of photomultipliers, a first group of photomultipliers of energy equal in number to the number of elementary detectors, and a second group of photomultipliers of determination of rank, equal in number to the number of crystals in each elementary detector.

According to other characteristics of the invention:

each photomultiplier in the first group is connected to each of the crystals of an elementary detector by a glass-fiber link, each photomultiplier in the second group is connected to a crystal of the same same rank in each elementary detector by a glass-fiber link, all the photomultipliers are connected electrically to a primary computer that delivers digital signals of energy and position of each photon detected, to the computer whose function is to reconstruct the tomographic images, the photomultipliers in the first group are calibrated to deliver a signal proportional to the energy of the photons emitted by a crystal, the photomultipliers in the second group are provided to deliver a pulse identifying the rank of the corresponding crystal.

BRIEF DESCRIPTION OF THE DRAWINGS

The invention is described below with reference to the attached drawings in which:

FIG. 1 is a schematic representation of the arrangement of the elementary detectors in the example of an observation at eight incidences by means of a multiple detector according to the invention.

FIG. 2 is a symbolic diagram of the arrangement of the measuring apparatus relative to the elementary detectors in FIG. 1.

DESCRIPTION OF THE PREFERRED EMBODIMENTS

With reference to the drawing it can be seen that the multiple detector according to the invention is composed of a certain number of elementary detectors.

In the observation of an organ, an elementary detector is provided for each incidence and for each section.

In the example described, with eight incidences and five sections, there are thus forty elementary detectors. The elementary detectors of the first section are numbered from 1 to 8, each of them corresponds to one incidence.

An elementary detector appears in the form of a bar constituted by a certain number of juxtaposed crystals, thirty-two for example. Each of these crystals is, for example, a square 8 mm on a side. The bars 1, 2 and 3 in FIG. 2 correspond to the elementary detectors 1, 2, 3 in FIG. 1 and are the only ones shown. Each crystal on a bar bears a reference corresponding to its rank. Thus crystal 15 is the fifth crystal in bar 1, and crystal 25 the fifth crystal in bar 2, and so on.

According to the invention, each crystal in a bar is connected to two photomultipliers of different types: an energy-measurement photomultiplier such as 51, 52, 53; and a photomultiplier determining the rank of the crystal such as 61, . . . 65.

The link between crystal and photomultiplier is advantageously embodied by glass fibers 16 since the photomultiplier must receive the light energy emitted by the scintillation of the crystal under the influence of the gamma rays emitted by the organ to be observed which is placed in the center of FIG. 1 so that it can be seen simultaneously at the eight incidences provided, and in the five sections provided.

Thus the photomultiplier of energy 51 receives the light signals from all the crystals on the bar 1, and the photomultiplier 61, determining the rank of the crystal, receives the signals from all the crystals of rank 1. In the example of embodiment proposed, in which eight incidences and five sections are provided, there are, thus, forty bars such as 1, 2 and 3. Each bar in turn has thirty-two crystals. Thus there are forty photomultipliers of energy such as 51, and thirty-two photomultipliers of determination of rank such as 61. The set of photomultipliers is connected electrically to the primary computer 70 which has a multiple role. First of all it conducts a spectrometry from the photomultipliers of energy, taking into account only the photons whose energy lies between two limits selected by the user as a function of the radio-element used, in order to eliminate diffused radiation. Then for each photon adopted it calculates the position of the crystal that detected this photon, from signals from the photomultipliers of energy and photomultiliers of rank. And finally, for each photon detected, it furnishes, in digital form, to the computer 71 charged with the reconstruction of the tomographic sections, the four quantities: energy, number of section number of incidence and rank of the crystal.

When a gamma ray strikes a crystal such as 25, that is to say the crystal of rank 5 on bar 2, this crystal scintillates and emits a photon of predetermined energy. The photomultiplier of energy 52 delivers a signal proportional to the energy of the photon. Photomultiplier 65 of determination of rank, delivers a pulse identifying the rank of the crystal 25. The coincidence of the energy signal and the rank pulse enables the primary computer 70 to locate the crystal with precision. Note that the energy signal is proportional to the energy of the photon.

The primary computer 70 delivers digital signals of energy and position of each photon detected, to computer 71, charged with the reconstruction of tomographic images.

According to the invention, the multiple detector is constituted by a certain number of elementary detectors or bars, which in turn are constituted by a certain number of juxtaposed crystals. Since these elementary detectors are disposed geometrically around the organ to be observed, to see it at a number of incidences, it is possible by a single measurement to obtain all the incidences and all the sections desired. This stationary period of the apparatus is therefore considerably shorter then that of a rotating gamma-camera.

Moreover, the fact of providing two groups of photomultipliers with different functions makes it possible to reduce the number of photomultipliers to a substantial extent while retaining a remarkable quality of measurement.

If it proves necessary to enhance the precision of measurement it is possible to assign the groups of photomultipliers of energy to just half of the crystals on the bars, that is to say, to provide two of them for each bar, and, furthermore, double the number of photomultipliers of rank by assigning each one to just half of the number of bars. This doubling of the number of photomultipliers is in no way incompatible.

And finally, another advantage of the multiple detector according to the invention is its modularity. It is possible, as a matter of fact, to increase or diminish the number of elementary detectors as a function of the organ studied (heart, brain, liver) and have the desired number of sections incidences. This multiple and modular detector permits a simultaneous registration of all the incidences of all the sections; it is particularly well suited to tomoscintigraphy.

What is claimed is:

1. Multiple detector for tomoscintigraphy of the sensitive-crystal, single-incidence type, having elementary detectors whose number corresponds to the product of the number of incidences times the number of sections, to receive simultaneously all the incidences of all the sections desired, each elementary detector being constituted by a bar with a certain number of juxtaposed crystals and oriented to receive one incidence of a predetermined section, the improvement being that is comprises a first and a second group of photomultipliers, said first group of photomultipliers being equal in number to the number of elementary detectors and comprising means for determining energy and said second group of said photomultipliers being equal in number to the number of crystals of each elementary detector and comprising means for determining rank, said multiple detectors being stationary during measurement.

2. Detector according to claim 1, wherein each photomultiplier in the first group is connected to each of the crystals of an elementary detector by a glass fiber link.

3. Detector according to claim 1, wherein each photomultiplier of the second group is connected to a crystal of the same rank of each elementary detector by a glass fiber link.

4. Detector according to claim 1, wherein all the photomultipliers are connected electrically to a primary computer means that delivers digital signals of energy and position of each photon detected to a computer charged with the reconstruction of the tomographic images.

5. Detector according to claim 1, wherein the photomultipliers of the first group are calibrated to deliver a signal proportional to the energy of the photons emitted by a crystal.

6. Detector according to claim 1, wherein the photomultipliers in the second group include means to deliver a pulse identifying the rank of the corresponding crystal.

* * * * *